(12) United States Patent
Shirado et al.

(10) Patent No.: US 8,972,054 B2
(45) Date of Patent: Mar. 3, 2015

(54) ROBOT APPARATUS, INFORMATION PROVIDING METHOD CARRIED OUT BY THE ROBOT APPARATUS AND COMPUTER STORAGE MEDIA

(75) Inventors: Hirokazu Shirado, Kanagawa (JP); Masakuni Nagano, Chiba (JP); Wataru Kokubo, Tokyo (JP); Yoshiaki Iwai, Tokyo (JP); Satoru Shimizu, Tokyo (JP)

(73) Assignee: Sony Corporation, Tokyo (JP)

( * ) Notice: Subject to any disclaimer, the term of this patent is extended or adjusted under 35 U.S.C. 154(b) by 896 days.

(21) Appl. No.: 13/070,138

(22) Filed: Mar. 23, 2011

(65) Prior Publication Data

US 2011/0238212 A1    Sep. 29, 2011

(30) Foreign Application Priority Data

Mar. 26, 2010 (JP) ................. 2010-073032

(51) Int. Cl.
*B25J 13/00* (2006.01)
*G05D 1/02* (2006.01)
*G06K 9/00* (2006.01)
(Continued)

(52) U.S. Cl.
CPC .......... *G05D 1/0274* (2013.01); *G06K 9/00335* (2013.01); *G06K 9/00771* (2013.01); *A61B 5/1112* (2013.01); *A61B 5/1113* (2013.01); *A61H 3/06* (2013.01); *G01S 19/14* (2013.01);
(Continued)

(58) Field of Classification Search
CPC . G05D 1/0274; G05D 1/0238; G05D 1/0246; G05D 2201/0206; A61B 5/1112; A61B 5/1113; A61H 3/06; G01S 19/14; G06K 9/00335; G06K 9/00771
USPC .................................. 700/245, 246, 257, 250
See application file for complete search history.

(56) References Cited

U.S. PATENT DOCUMENTS

2006/0241812 A1   10/2006 Jung
2007/0198128 A1*   8/2007 Ziegler et al. ................. 700/245
2007/0294106 A1   12/2007 Alsafadi

FOREIGN PATENT DOCUMENTS

CN    1853876 A    11/2006
CN    1911606 A    2/2007
(Continued)

OTHER PUBLICATIONS

Lim, M. Y., Aylett, R., Ho, W. C., Enz, S., & Vargas, P. (Jan. 2009). A socially-aware memory for companion agents. In Intelligent Virtual Agents (pp. 20-26). Springer Berlin Heidelberg.*
(Continued)

*Primary Examiner* — Khoi Tran
*Assistant Examiner* — Adam Mott
(74) *Attorney, Agent, or Firm* — Oblon, McClelland, Maier & Neustadt, L.L.P.

(57) ABSTRACT

A robot apparatus, method and computer program storage device use a memory that stores cueing point information and user information to assist a user in an external environment. The cueing points are distributed within an environmental map held by the robot apparatus, and when the user is detected by the robot apparatus as approaching a predetermined region within the external environment classified as a cueing point, the robot apparatus reacts by providing a cue to the user. The cue may user-specific, or optionally provided based on a level of care required by the user.

24 Claims, 7 Drawing Sheets

(51) Int. Cl.
  *A61B 5/11* (2006.01)
  *A61H 3/06* (2006.01)
  *G01S 19/14* (2010.01)

(52) U.S. Cl.
  CPC ............ *G05D1/0238* (2013.01); *G05D 1/0246* (2013.01); *G05D 2201/0206* (2013.01)
  USPC ........................................................ 700/250

(56) References Cited

FOREIGN PATENT DOCUMENTS

| | | | |
|---|---|---|---|
| CN | 101002209 | A | 7/2007 |
| CN | 201267592 | Y | 7/2009 |
| JP | 2004-243504 | | 9/2004 |
| JP | 2005-103679 | A | 4/2005 |
| JP | 2007-102488 | | 4/2007 |
| JP | 2008-142876 | A | 6/2008 |
| JP | 2008-254122 | A | 10/2008 |
| JP | 2008-260107 | A | 10/2008 |
| JP | 2009-136987 | A | 6/2009 |

OTHER PUBLICATIONS

Combined Chinese Office Action and Search Report issued Jul. 10, 2014 in Patent Application No. 201110069128.X (with English language translation).

Japanese Office Action issued Feb. 4, 2014 in Patent Application No. 2010-073032.

* cited by examiner

| Position | Level | Contents |
|---|---|---|
| (230, 65) | 1 | Toilet |
| (190, 130) | 3 | Convex |
| (220, 170) | 3 | Convex |
| (130, 180) | 2 | Block |

FIG.6

| User | Level |
|---|---|
| (U1) | 3 |
| (U2) | 1 |
| (U3) | 0 |

ROBOT APPARATUS, INFORMATION PROVIDING METHOD CARRIED OUT BY THE ROBOT APPARATUS AND COMPUTER STORAGE MEDIA

BACKGROUND

1. Technical Field

The present disclosure relates to a robot apparatus, an information providing method carried out by the robot apparatus, and a computer storage media having instructions that when carried out by a processor cause the processor to perform the method.

2. Description of the Related Art

In care-giving and medical scenes, for example, a care-giver or a nurse may visually or audibly give a cue to a behavior of a person who receives the care or nursing service. This cueing provides notification about a matter which the person may not notice, so as to warn the person in advance. For example, when there is a step in a house, a cue may be given from the care-giver to the care-receiver, whereby the care-receiver can avoid hazards such as tripping and falling.

In a technique used in the past, instead of a care-giver gives a cue, a care-receiver wears a monitoring/warning device around his/her neck and the like, which gives a cue to a behavior of the care-receiver. In another technique, an environmental installation-type sensor, such as a monitoring camera fixed to one position, recognizes a care-receiver, and a cue is given to a behavior of the recognized person.

Further, in the technical field of robots, there is a technique disclosed by Japanese Patent Application Laid-Open No. 2007-102488, for example. In this technique, an autonomous mobile apparatus follows a particular person, and recognizes the particular person and an ambient environment. The autonomous mobile apparatus determines the degree of danger of the particular person, and when the particular person is determined to be in danger, the degree of danger is reduced.

Japanese Patent Application Laid-Open No. 2004-243504 discloses a technique for controlling a drive mechanism which executes operation at a point based on operation support information attached to the point that serves as a mark of a destination of movement that is set in advance in a work space in order to reduce the burden imposed on information processing performed by a robot.

SUMMARY

However, when the care-receiver wears the monitoring/warning device around his/her neck and the like, the present inventor recognized there is a problem in that the monitoring/warning device imposes a burden on the care-receiver. On the other hand, when the camera fixed to one position is used, there is a problem in that the camera can recognize only a limited range, and the camera is unable to recognize a behavior of a person in a dead space.

Further, since the degree of danger in the ambient environment varies according to a physical ability and the like of a person, the degree of danger varies according to each person receiving a cue given by the autonomous mobile apparatus. Therefore, if the autonomous mobile apparatus performs an operation to move in front of a person or emit a warning beep in advance in order to reduce the degree of danger, there is a problem in that this operation is unnecessary and cumbersome for a person who can predict the degree of danger by himself/herself.

Moreover, in a case where the autonomous mobile apparatus does not store the ambient environment in advance, and successively recognizes the ambient environment, there is a problem in that the autonomous mobile apparatus may not give any cue at all to a behavior of a person regarding a previously unrecognized ambient environment. In this case where the autonomous mobile apparatus does not store the ambient environment, there is a problem in that a cue may not be given to a behavior of a person in a dead space that may not be recognized by the autonomous mobile apparatus.

In view of the foregoing, it is desirable to provide a novel and improved robot apparatus and a novel and improved information providing method, and associated computer program storage device, carried out by the robot apparatus, wherein information about an ambient environment can be appropriately provided according to a recognized user.

In a non-limiting context, an exemplary robot apparatus (and an associated method that employs the robot apparatus and computer program storage device that is used in the robot apparatus) use a computer storage device. The computer program storage device stores cueing point information and user information. The cueing point information includes position information and level of care information associated with the position information. The user information includes identification information of a user and user-specific level of care information. The robot apparatus also includes a determining unit configured to decide to issue a cue based on at least the cueing information and the user information. Likewise, a method for using the robot, as well as a computer program storage device having instructions that program a processor to perform the method have similar features, as well as optional features like those discussed below in the context of the robot apparatus.

The robot apparatus may also include a user recognition unit configured to recognize the user. In this case, the determining unit determines the user-specific level of care based on a recognition made by the user recognition unit.

The robot apparatus may also include a recording mechanism configured to record an environmental map. Also, cueing point information for corresponding cueing points are associated with predetermined regions within the environmental map.

The robot apparatus may also include a user recognition unit configured to recognize a position of the user. In this situation, the determining unit is configured to determine a cue to be given when the position of the user is in a predetermined range of a corresponding cueing point.

The robot apparatus may also include a behavior recognition unit configured to recognize a behavior of the user, and a prediction unit configured to predict a future behavior of the user based on a present behavior of the user as recognized by the behavior recognition unit. In this situation, the determining unit determines a cue to be given based the future behavior of the user as predicted by the prediction unit and a corresponding cueing point.

The robot apparatus may also include a cue generation mechanism that generates at least one of an audio cue and a visual cue depending on the user information.

The robot apparatus may optional include a drive unit configured to move the robot apparatus. A controller is used to issue a movement command to operate the drive unit to move the robot toward the position of the user as recognized by the user recognition unit.

DETAILED DESCRIPTION OF THE EMBODIMENT(S)

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

The explanation will be made in the order listed below.
1. Configuration of embodiment
2. Operation of embodiment
<1. Configuration of Embodiment>

Figure 1:
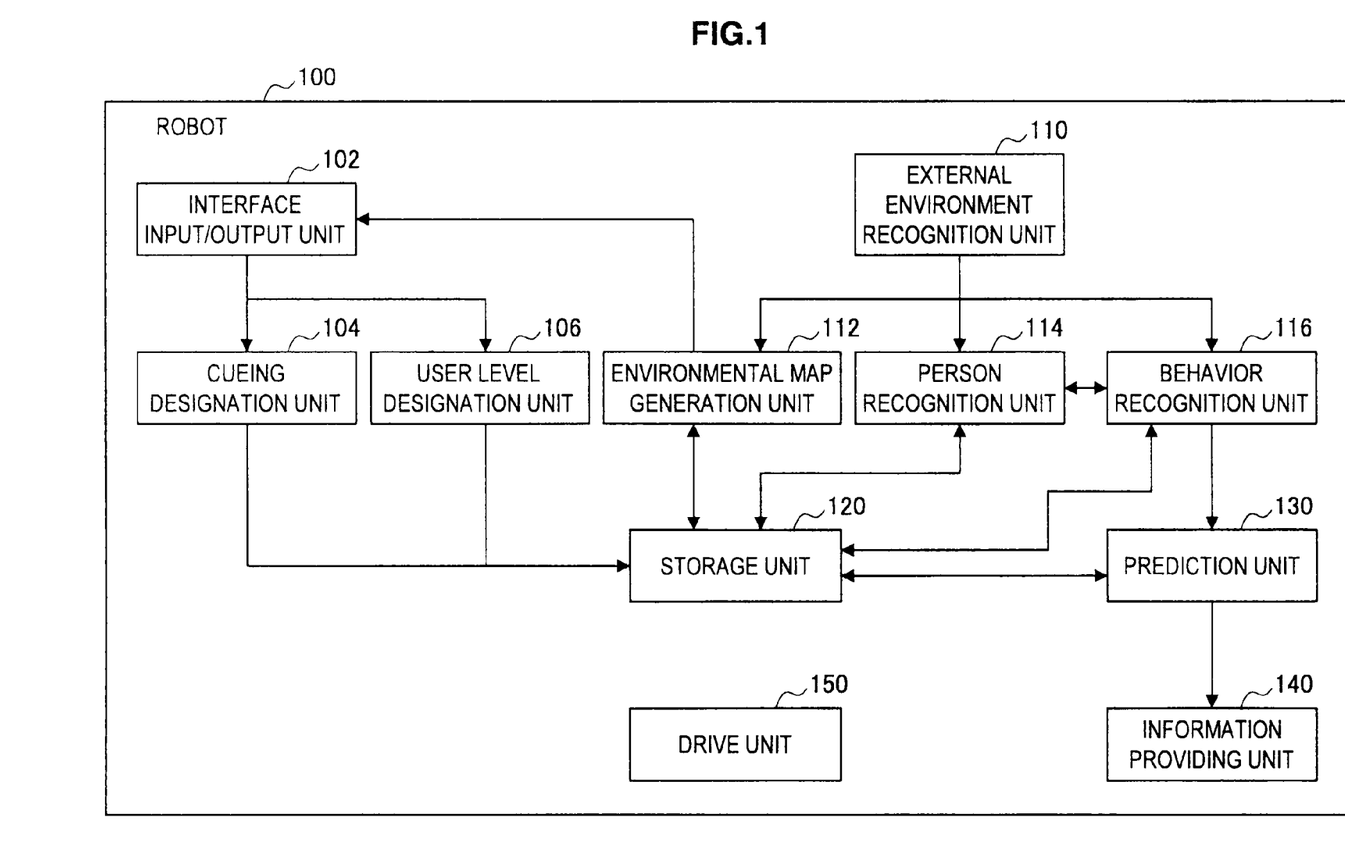
FIG. 1 is a block diagram illustrating a robot 100 according to an embodiment of the present invention.

First, a robot 100 according to an embodiment of the present invention will be explained with reference to FIG. 1. FIG. 1 is a block diagram illustrating the robot 100 according to the present embodiment.

The robot 100 recognizes an external environment, autonomously moves according to the recognized environment, and performs an action for a user. The robot 100 according to the present embodiment generates an environmental map. Then, the robot 100 determines a behavior of the user, and provides information, e.g., gives a cue to the user in a visual or audible manner. In order to give a cue, the robot 100 stores a cueing point at which a cue is to be given. The cueing point corresponds with a location within the external environment and reflected in a region of the environmental map.

Therefore, the robot 100 can notify the user of an operation which is to be performed by the user in advance of the user actually arriving at the point of interest, for example cueing the user as the user approaches a step down. The robot 100 determines whether a cue is to be given and determines the type of the cue according to a property of the user such as physical ability of the user.

The robot 100 can generate an environmental map covering a wide area by moving around, and stores in computer readable storage device the generated environmental map. In addition, the robot 100 previously sets cueing points in the environmental map. Therefore, compared with a case where the robot 100 successively recognizes the ambient environment, the robot 100 is less likely to fail to recognize the ambient environment, and accordingly, the robot 100 can give cues to behaviors of the user more often. In addition, the robot 100 can give a cue even to a behavior of a person in a dead space (not in line-of-sight) which may not be recognized from a current location of the robot 100.

For example, in a case of a room, examples of points at which cues should be given and examples of points at which cues are preferably given include a narrow portal through which a person passes, a step portion, a door, and a bed. The robot 100 gives a warning to a person approaching the portal and a person in the portal so that the person avoids collision, tripping, and falling. For example, the cueing point may be a wheel chair. In this case, according to a behavior of the user, the robot 100 reminds the user not to forget to apply a brake when the user sits on a wheelchair. Alternatively, the cueing point may be a toilet. In this case, the robot 100 reminds the care-receiver to pull up and down his/her trousers.

As shown in FIG. 1, the robot 100 includes, for example, an interface input/output unit 102, a cueing specifying unit 104, a user level specifying unit 106, an external environment recognition unit 110, an environmental map generation unit 112, a person recognition unit 114, a behavior recognition unit 116, a storage unit 120, a prediction unit 130, an information providing unit 140, and a drive unit 150.

For example, the robot 100 has a microprocessor, which controls, the interface input/output unit 102, the external environment recognition unit 110, the storage unit 120, the information providing unit 140, and the drive unit 150 and the like. Further, the microprocessor includes, for example, the cueing specifying unit 104, the user level specifying unit 106, the environmental map generation unit 112, the person recognition unit 114, the behavior recognition unit 116, and the prediction unit 130.

The interface input/output unit 102 is an operation unit with which various kinds of data are input by a user and the like who uses the robot 100. The interface input/output unit 102 is also a display unit having a display screen, which displays a video to the user. For example, the interface input/output unit 102 displays the environmental map on the display screen. Then, the interface input/output unit 102 is used by the user to input a cueing point to the environmental map and input user information. Optionally, the robot may respond to a "come here" audible command, IR or RF command. The robot moves to the source of the command, near the user, which would enable the user to view a helpful video that may assist the user with a particular activity.

The cueing specifying unit 104 is an example of an information providing point specifying unit, and receives information about cueing points from the interface input/output unit 102. The input/output unit 102 includes a wireless transceiver that communications with wireless portable (or non-portable) devices such as smartphones, tablet computers, or other wireless devices for exchanging information such as setting cues. Then, the cueing specifying unit 104 associates the information about the cueing points with information about the environmental map, and specifies the cueing points in the environmental map. Further, the cueing specifying unit 104 specifies coordinate information about the cueing points as well as cueing levels and names of cueing points.

The user level specifying unit 106 is an example of a user administration unit, and receives information about users from the interface input/output unit 102. Then, the user level specifying unit 106 registers a plurality of users which are receiver of cues, and sets cueing levels of respective users. In the present embodiment, cues are given according to the physical abilities of the users rather than cues are given to all the users at the cueing points. For example, the cueing levels are set for not only the cueing points but also the users. Accordingly, both of the cueing points and the users are associated with each other, and an adjustment is made as to whether cues are given or not. When the cueing levels are set, whether cues are give or not can be easily set for each user.

Generally, the method for setting whether cues are given or not is not limited to the setting of the cueing levels. For example, at each cueing point, the users may be set, one by one, as the receiver of cues. The cueing points and the users who are receivers of cues may not simply be classified according to the magnitudes of levels, but may be classified into genres such as behavior patterns and time patterns, for example, "household chores", "walking movement", and "time period in daytime."

The external environment recognition unit 110 is, for example, a stereocamera and a distance sensor, and obtains and recognizes information about the external environment of the robot 100. The external environment recognition unit 110 sends information about the external environment to the environmental map generation unit 112, the person recognition unit 114, and the behavior recognition unit 116.

The environmental map generation unit 112 generates the environmental map using a technique such as SLAM (Simultaneous Localization and Mapping) based on the information about the information about the external environment. The environmental map is updated successively (i.e., an update is triggered by a predetermined time period), and the environmental map generation unit 112 may allow tracking of an object existing in the external environment may be tracked. When the cueing points are specified in the environmental map, the cueing points are also tracked.

The person recognition unit 114 detects a person and identifies the detected person based on the user information registered in the storage unit 120 and the information about the external environment.

The behavior recognition unit 116 calculates a position and a moving direction of a person recognized by the person recognition unit 114. The behavior recognition unit 116 transmits, to the prediction unit 130, the calculated information about the position and the moving direction of the person. Further, the behavior recognition unit 116 recognizes a behavior of a person based on behavior patterns of the person recorded in the storage unit 120 and the information about the external environment. Then, the behavior recognition unit 116 transmits the behavior of the recognized person to the prediction unit 130.

The storage unit 120 is, for example, a memory, which records the generated environmental map, the cueing points, and the user information. Further, the storage unit 120 stores various kinds of programs and information used for the person recognition performed by the person recognition unit 114 and the behavior recognition performed by the behavior recognition unit 116. The information used for each processing is read from the storage unit 120.

The prediction unit 130 predicts a behavior of a person by calculating whether a person is close to a cueing point or not based on the position and the moving direction of the person and the cueing points. In addition, the prediction unit 130 predicts how the person subsequently behaves based on the behavior of the recognized person. The prediction unit 130 transmits the predicted behavior to the information providing unit 140.

The information providing unit 140 is arranged in the robot 100, and the information providing unit 140 gives a cue to the user based on the information about the user and the predicted behavior. Examples of cues include a light emission of a lamp which can be recognized by the user, an image display on a display screen, and an audio output which can be audibly recognized by the user. The content of cue may be changed according to the user based on the cueing level set for each user. However, the present invention is not limited to a case where the information providing unit 140 is installed in the robot 100. For example, the robot 100 may include a communication unit, and the robot 100 may give a cue to a user by transmitting information about the cue to a portable apparatus such as a portable telephone and causing the portable apparatus to receive a mail and provide vibration to the user.

The drive unit 150 enables movement and operation of the robot 100. The drive unit 150 drives the robot 100 based on a signal autonomously generated by the robot 100 itself, or drives the robot 100 based on a signal generated by an operation of a user.

<2. Operation of Embodiment>

Subsequently, operation of the robot 100 according to the present embodiment will be explained.

[Cueing Preparation Processing]

Figure 2:
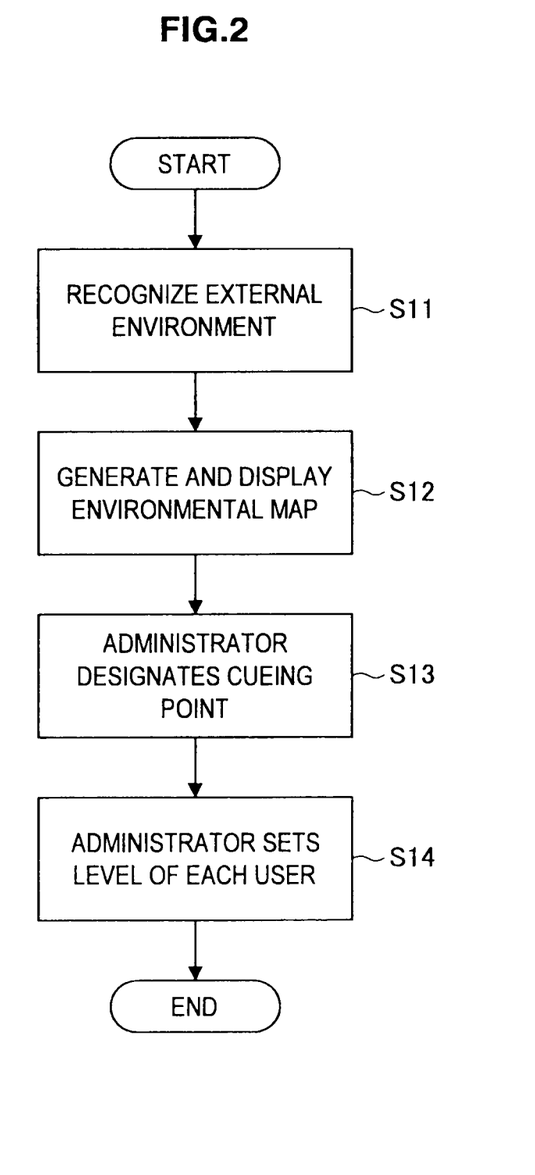
FIG. 2 is a flowchart illustrating a cueing preparation processing of the robot 100 according to the embodiment.

First, cueing preparation processing of the robot 100 according to the present embodiment will be explained. FIG. 2 is a flowchart illustrating a cueing preparation processing of the robot 100 according to the present embodiment.

First, the robot 100 recognizes the external environment (step S11). When the robot 100 recognizes the external environment, the robot 100 can obtain information about a shape, a position, a texture, a color, and the like of an object outside of the robot 100. The robot 100 successively obtains the information while moving around.

Subsequently, the robot 100 generates the environmental map based on the obtained information about the external object (step S12). In a case where the robot 100 recognizes a new external environment, the robot 100 generates a new environmental map, and records the generated environmental map to the storage unit 120. When the environmental map recorded in the storage unit 120 matches the external environment recognized this time, the recorded environmental map is updated. Then, the generated environmental map is transmitted to the interface input/output unit 102, and the display screen displays the environmental map (step S12).

Thereafter, for example, an administrator of the robot 100 sees the environmental map displayed on the display screen, and the administrator specifies the cueing points in the environmental map (step S13). The cueing points are points (or locations) at which cues should be given or points at which cues are preferably given by the robot 100 at appropriate locations in a room. Coordinate information of the cueing points specified in the environmental map are recorded to the storage unit 120 together with locations at which cues are given, names of objects, cueing methods, cueing levels, and the like.

The cueing level, which is a component of level of care information, is a level for classifying cueing points according to a user receiving cues. For example, when the cueing level of the cueing points is set to a low level, cues are given to all the users. On the contrary, when the cueing level of the cueing points is set to a high level, cues are given only to persons having low physical ability such as elderly people. Thus, an aspect of level of care information associated with a particular cueing point may include the cueing level for that cueing point and the cueing information itself. For example at least some cue is given for all users if the cueing level is set low. However, even more information may be given at that cueing point if the user-specific level of care associated with a particular user indicates more information, or unique information, is associated with users having user-specific levels of care that demand that level of additional information. On the other hand, if another cuing point has a higher (or different) cueing level, then the level of care information may be minimal (or non-existent), and only provided to specific users that require some assistance in that situation, as quantified by their user-specific level of care information. This approach allows for particular cueing points to have level of care information associated therewith, which permits the association of obstacles and other locations within an environmental map into discrete groups that can be classified with common levels, all as part of level of care information. Likewise, users themselves can have user-specific levels of care associated with them so that the amount of information provided to that user when confronted with a particular cueing point can be adapted to that user. An elderly person may have one user-specific level of care associated with them, while a child may have a different user-specific level of care associated with them. As a consequence, the cue given to the particular person for a particular cueing point will be determined by the level of care information associated with the cueing point, as well user-specific level of care information associated with that user.

The method for specifying the cueing points may be a method for inputting the cueing points using a finger, a stylus, and the like when the display screen is a touch panel, or may be a method for inputting the cueing points with a mouse and a keyboard. The cueing points may optionally be input audibly, by having the robot move to a particular cueing point, or observe the user at a particular cueing point. The cueing point may then be marked either with a tactile command through a user interface or via an audible command received through a microphone and audio processing circuit. Likewise the user may have an IR or RF remote control that sets cueing points when the user is at certain locations. For example, the user can carry the remote control (or other portable wireless device, such as a smartphone, or tablet computer) with him, and when he remembers that he would like a cue at a certain spot, the user can press a button on the remote control, which triggers the robot to create a new cueing point. A wireless signal from the portable wireless device includes position information and other information describing a request for establishing a cueing point. User information, such as identification information, and user-specific level of care information, may be entered to correspond with the cueing point. It should also be stated that the user-specific level of care may be unique to a particular user, or may be one of a plurality of gradations, such as one of three different levels.

Then, the users who receive cues from the robot 100 are input by the administrator, and are recorded to the storage unit 120. For example, facial information, bodily information, and the like of users are recorded. Further, which cueing level is used to give cues to a user is set for each of the recorded users (step S14). For example, a low cueing level is set for a young person who hardly needs any cues, and a high cueing level is set for an elderly person who has a lower level of attention.

The preparation processing for cueing is completed with the above steps.

[Cueing Processing]

Figure 3:
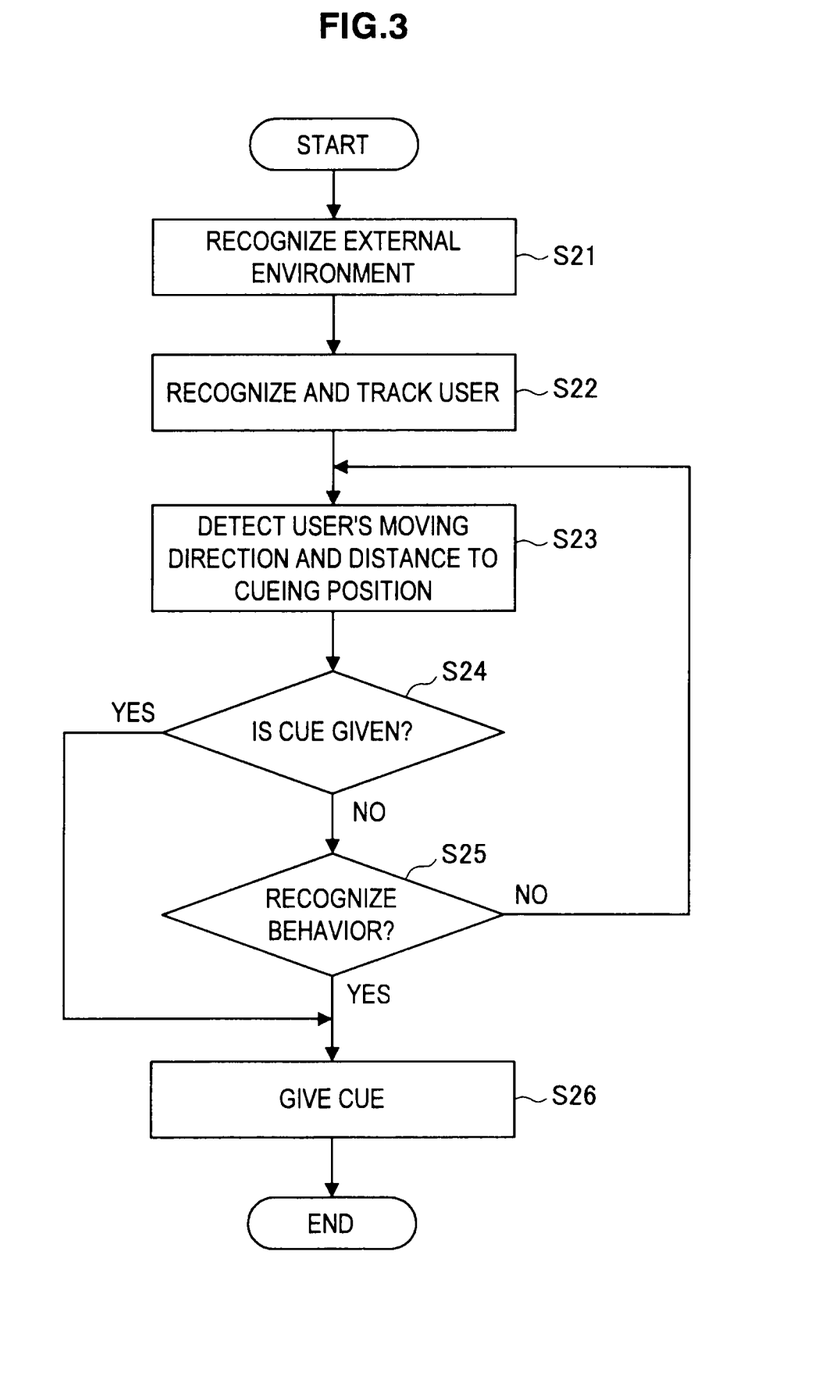
FIG. 3 is a flowchart illustrating a cueing processing of the robot 100 according to the embodiment.

Subsequently, the cueing processing of the robot 100 according to the present embodiment will be explained. FIG. 3 is a flowchart illustrating a cueing processing of the robot 100 according to the present embodiment.

First, the robot 100 recognizes an external environment (step S21). When the robot 100 recognizes the external environment, the robot 100 can obtain information about a shape, a position, a texture, a color, and the like of an object outside of the robot 100. Further, the robot 100 can obtain information about a face or a movement of a user by recognizing the external environment.

Subsequently, the obtained information about the user is collated with the previously registered information about the user (for example, facial information and bodily information), whereby the user is recognized. Further, the recognized user is tracked (step S22).

Then, the robot 100 calculates a position and a moving direction of the user in the environmental map, and detects a distance between the user and a cueing point (step S23). The robot 100 successively detects the distance between the user and the cueing point, whereby the robot 100 can find, for example, whether the user approaches the cueing point or not and how many seconds or more the user stays at the cueing point.

Then, the robot 100 determines whether a cue is to be given or not based on the moving direction of the user and the distance between the user and the cueing point (step S24). When the robot 100 determines that a cue is to be given, the robot 100 gives a cue (step S26). At this moment, in a case where the robot 100 is at a position at which the robot 100 may not directly recognize the cuing point in the environmental map, the robot 100 can find the relationship between the user and the cueing point in the environmental map. Therefore, the robot 100 can give a cue to the user.

On the other hand, when the robot 100 determines that no cue is to be given based on the moving direction of the user and the distance between the user and the cueing point, the robot recognizes a behavior of the user, and determines whether the behavior of the user matches a previously registered behavior pattern (step S25). In a case where the robot 100 recognizes a behavior matching the previously registered behavior pattern as a result of the behavior recognition or where the robot 100 predicts that the user may perform a predetermined behavior in the future based on the behavior recognition, the robot 100 gives a cue (step S26). On the other hand, in a case where the robot 100 recognizes no behavior matching the previously registered behavior pattern as a result of the behavior recognition or where the robot 100 does not predict that the user may perform the predetermined behavior, the robot 100 returns back to step S23 to repeat detection of cueing conditions.

One set of cue processing is completed with the above steps. As long as the cuing processing continues without halt, the above processing operation is repeated, so that the robot 100 gives cues based on the relation between the user and the cueing point and the behavior of the user.

[Setting of Cueing Point]

Figure 4:
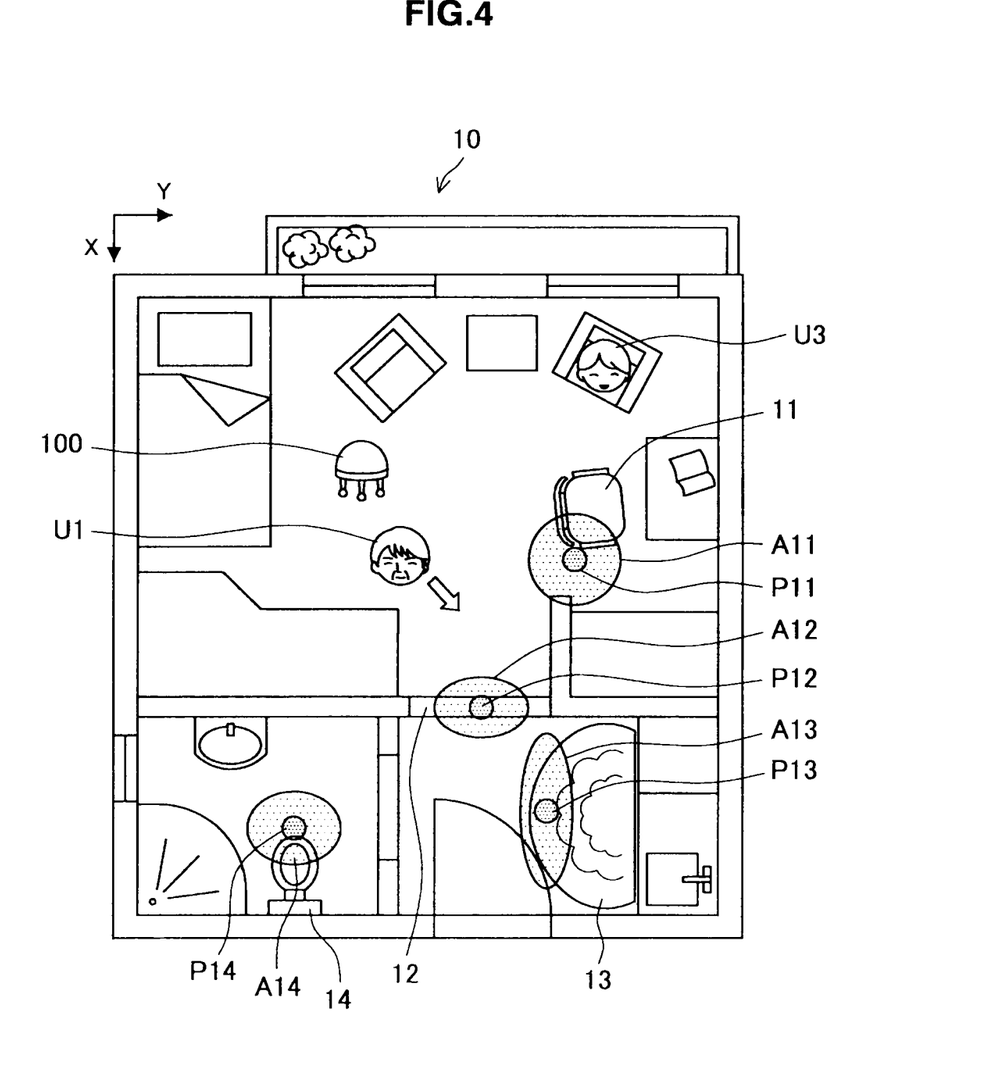
FIG. 4 is an explanatory diagram illustrating an environmental map 10 generated by the robot 100 according to the embodiment.

Subsequently, the settings of the cuing points will be explained in detail with reference to FIGS. 4 and 5. When a bird's eye view mode is chosen for the generated environmental map, the environmental map is displayed as shown in FIG. 4, for example. FIG. 4 is an explanatory diagram illustrating an environmental map 10 generated by the robot 100. The environmental map 10 of FIG. 4 shows a room. Furniture, users U1, U3, the robot 100, and the like are displayed in the environmental map 10.

While the environmental map is displayed on the display screen, the administrator specifies, for example, cueing points P11, P12, P13, P14, and the like. A chair is specified by P11. A step of a threshold is specified by P12. A step of a carpet is specified by P13. A toilet is specified by P14. Alternatively, the cueing points may not be point information, and areas P11, P12, P13, P14 each having a predetermined size of area may be specified as the cueing points.

Figure 5:
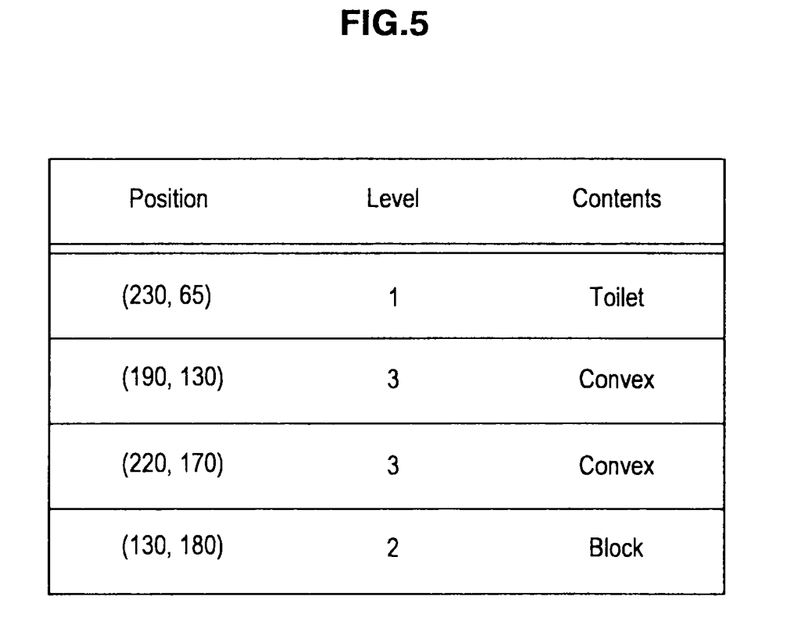
FIG. 5 is a table showing information about a cueing point.

Further, not only the coordinate information of the cuing points but also the names of the cuing points and the cueing levels are set as shown in FIG. 5. FIG. 5 is a table showing information about the cuing points. For example, when cues are given to all the persons, level 1 is set. When cues are given only to elderly people and the like, level 3 is set.

[Registration of User]

Figure 6:
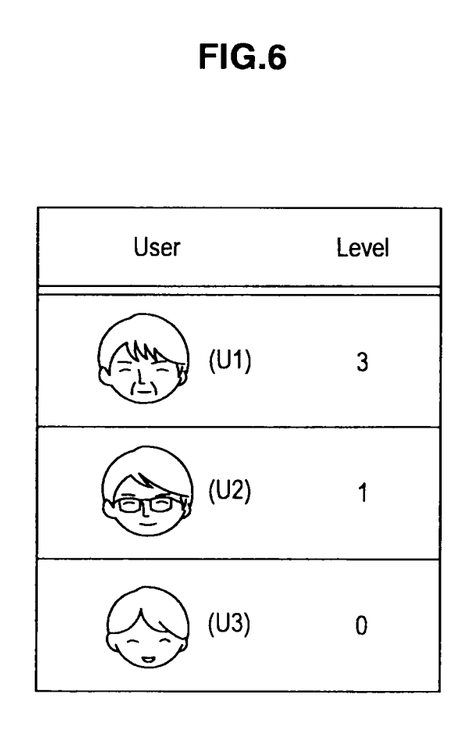
FIG. 6 is a table showing information about users.

Subsequently, registration of a user will be explained with reference to FIG. 6. FIG. 6 is a table showing information about users. As shown in FIG. 6, image information of facial information and the like of a user, a user ID, a user name, a cueing level, and the like are associated with each other and recorded. For example, the cueing level for elderly people (U1) is set as 3, and the cueing level for young people (U3) is set as 1.

[Behavior Recognition Processing]

Figure 7:
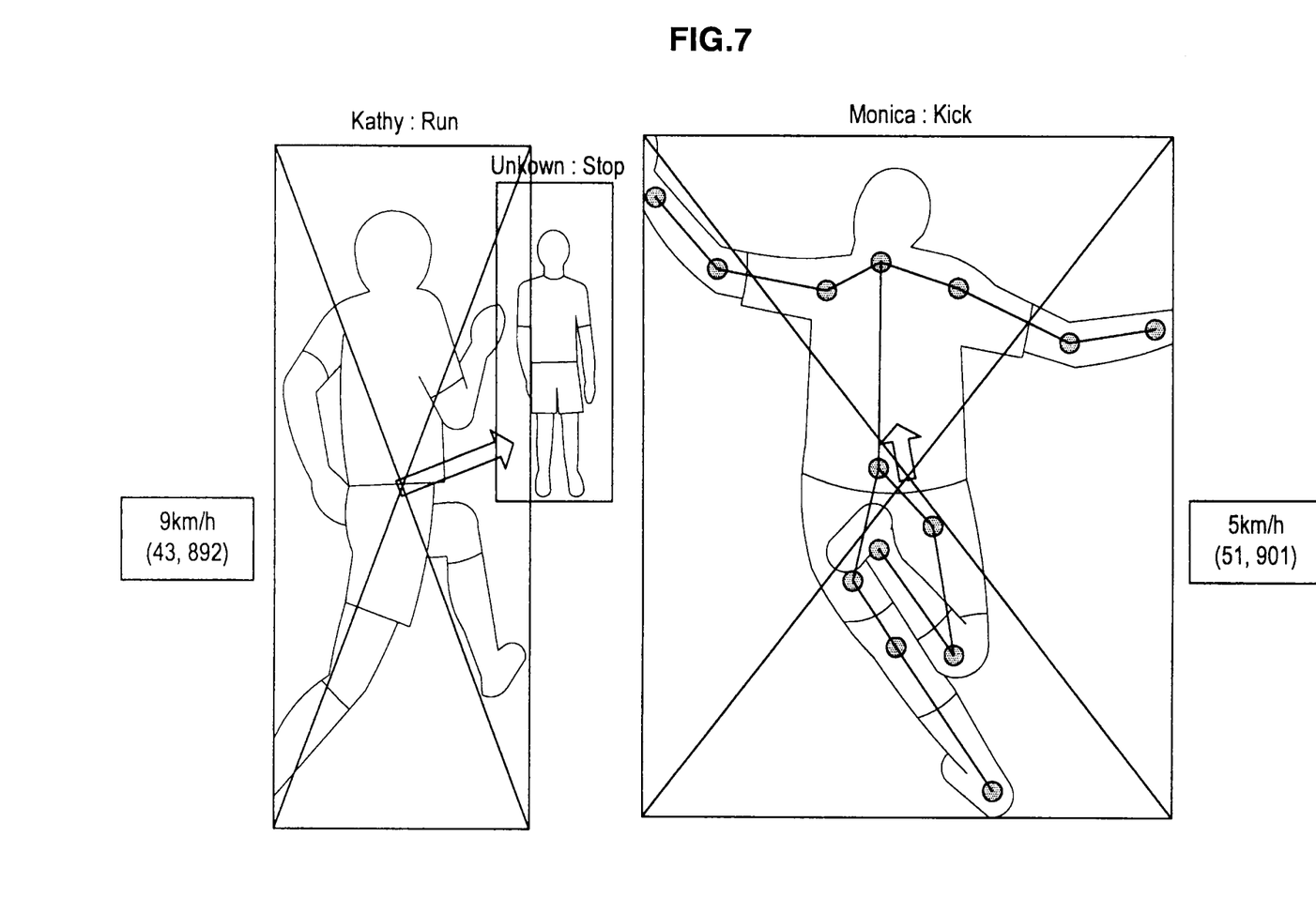
FIG. 7 is an explanatory diagram illustrating an example of result of a subject image and behavior recognition obtained by an external recognition.

Now, behavior recognition processing will be explained with reference to FIG. 7. FIG. 7 is an explanatory diagram illustrating an example of result of a subject image and behavior recognition obtained by an external recognition.

When facial recognition processing is carried out before the behavior recognition, a person obtained from the external environment recognition can be identified. In the example of FIG. 7, a person on the left is determined to be Kathy, and a person on the right is determined to be Monica. However, a person in the center has not yet been identified or may not be identified (unknown).

In the behavior recognition of the person, for example, feature points are extracted, and the extracted feature points are tracked, whereby how the person behaves can be found out. In the example of FIG. 7, it is recognized that the person on the left is running, and the person on the right is kicking. It is recognized that the person in the center is standing without walking.

In addition, a coordinate point in the center of the entire person is obtained. A current location and a moving speed of the person can be obtained by tracking in which direction the coordinate point is moving. The current location and the moving speed of the person may be calculated from the position, direction, and the moving speed of the face of the person. In the example of FIG. 7, it is recognized that a coordinate point (43, 892) of the person on the left is moving ahead to the right at 9 km/h, and a coordinate point (51, 901) of the person on the right is moving ahead to the left at 5 km/h.

How the recognized person subsequently behaves can be predicted, and a cue can be given to the predicted behavior for carrying out the person recognition processing as described above. As a result, a subsequent behavior can be recommended to the user in a shorter time or in advance.

As hereinabove described, according to the present embodiment, a cue is given from the robot 100 without imposing a burden on a user such as a care-receiver and the like. Further, since the robot 100 is moving around, the robot 100 can recognize a wide range, and the robot 100 can recognize a behavior of a person in a dead space by recording the environmental map.

Further, although the degree of danger in the ambient environment varies according to a physical ability and the like of a person, the robot 100 according to the present embodiment recognizes the user, and gives a cue according to the user. For example, a setting is made such that no cueing is given to a user who hardly needs any cueing. Therefore, since a user who can predict the degree of danger by himself/herself does not have to receive unnecessary cues, the user is not bothered by those unnecessary cues. On the other hand, since a setting is made such that a user who frequently needs cues receives cues in various situations, the user can appropriately receive benefits of cues.

Further, the robot 100 stores the environmental map. Therefore, the robot 100 can give a cue to a behavior of a person in a dead space which may not be recognized by the robot 100.

It should be understood by those skilled in the art that various modifications, combinations, sub-combinations and alterations may occur depending on design requirements and other factors insofar as they are within the scope of the appended claims or the equivalents thereof.

For example, in the above embodiment, the robot 100 uses a result of the recognition carried out in the external environment to identify a person. However, the present invention is not limited to this example. For example, the robot 100 may receive information transmitted from a GPS (Global Positioning System) device possessed by a person, and the robot 100 may find unique information of the person, positional information, and a moving direction of the person. Even when the robot 100 is at a position at which the robot 100 may not directly recognize the user, the robot 100 obtains information about the user from the GPS device, and can give a cue to the user based on a relationship with a cueing point in the environmental map.

In the above explanation of the embodiment, the users are registered to the robot 100. However, the present invention is not limited to this example. For example, the present invention can also be applied even in a case where cues are given to an indefinite number of people. For example, when a person has a distinguishing external appearance, i.e., a person is on a wheel chair, or a person is pushing a baby car, a cue may be given upon determining the external appearance without identifying the person.

The present application contains subject matter related to that disclosed in Japanese Priority Patent Application JP 2010-073032 filed in the Japan Patent Office on Mar. 26, 2010, the entire content of which is hereby incorporated by reference.

The invention claimed is:

1. A robot apparatus, comprising:
a computer program storage device that stores cueing point information and user information,
said cueing point information including position information and level of care information associated with said position information,
said user information including identification information of a user and user-specific level of care information associated with the identification information of the user;
circuitry configured to:
decide to issue a cue based on at least said cueing point information and said user information;
recognize said user and a position of the user; and
issue at least one of an audio cue and a visual cue when the circuitry decides to issue the cue, wherein
the circuitry decides to issue the cue by (a) identifying whether the position of the user identified by the circuitry is in a predetermined range of a corresponding cueing point based on the position information, (b) identifying the user-specific level of care information based on the identification information of the user identified by the recognizing by the circuitry, and (c) comparing the level of care information associated with the position information of the corresponding cueing point with the user-specific level of care information identified by the circuitry.

2. The robot apparatus of claim 1, wherein
said circuitry is configured to determine said user-specific level of care information based on a recognition made by the circuitry.

3. The robot apparatus of claim 1, wherein
the circuitry is configured to record an environmental map, wherein cueing point information for corresponding cueing points are associated with predetermined regions within said environmental map.

4. The robot apparatus of claim 3, wherein:
the circuitry is configured to record an update of the environmental map, said update being triggered by at least one of a predetermined time period and a change in content in said environmental map.

5. The robot apparatus of claim 1, wherein
the circuitry is configured to:
recognize a behavior of said user, and
predict a future behavior of said user based on a present behavior of said user as recognized by said circuitry; and
said circuitry determines the cue to be given based on the future behavior of said user as predicted by said circuitry and a corresponding cueing point.

6. The robot apparatus of claim 1, wherein:
the cue issued by said circuitry being classified into one of a plurality of patterns including behavior patterns and time patterns.

7. The robot apparatus of claim 1, further comprising:
a drive unit configured to move the robot apparatus; wherein
the circuitry is configured to issue a movement command to operate said drive unit to move the robot toward the position of said user as recognized by said circuitry.

8. The robot apparatus of claim 1, further comprising:
a receiver configured to receive wireless communication signals from a portable wireless device.

9. The robot apparatus of claim 1, further comprising:
a transmitter configured to transmit information about the cue to a portable wireless device.

10. An information providing method performed with a robot apparatus, comprising:
storing and subsequently retrieving from a computer program storage device cueing point information and user information,
said cueing point information including position information and level of care information associated with said position information,
said user information including identification information of a user and user-specific level of care information associated with the identification information of the user;
determining with a processor to issue a cue based on at least said cueing point information and said user information;
recognizing said user and a position of the user; and
issuing at least one of an audio cue and a visual cue when the processor decides to issue the cue, wherein
the determining is conducted by (a) identifying whether the position of the user identified by the recognizing is in a predetermined range of a corresponding cueing point based on the position information, (b) identifying the user-specific level of care information based on the identification information of the user identified by the recognizing, and (c) comparing the level of care information associated with the position information of the corresponding cueing point with the identified user-specific level of care information.

11. The method of claim 10, wherein
said determining step determines said user-specific level of care information based on a recognition made by the processor in said recognizing step.

12. The method of claim 10, further comprising:
recording an environmental map in said computer program storage device, wherein cueing point information for corresponding cueing points are stored in association with predetermined regions within said environmental map.

13. The method of claim 12, wherein:
said recording includes recording an update of the environmental map, said update being triggered by at least one of a predetermined time period and a change in content in said environmental map.

14. The method of claim 10, further comprising:
recognizing with the processor a behavior of said user, and
predicting a future behavior of said user based on a present behavior of said user as recognized by said processor; wherein
said determining step determines the cue to be given based on the future behavior of said user as predicted in said predicting step and a corresponding cueing point.

15. The method of claim 10, wherein:
the cue issued in said issuing being classified into one of a plurality of patterns including behavior patterns and time patterns.

16. The method of claim 10, further comprising:
issuing a movement command to move the robot toward the position of said user as recognized in said recognizing step; and
moving the robot apparatus with a drive unit in response to the movement command.

17. The method of claim 10, further comprising:
receiving from a portable wireless communication device a signal requesting a cueing point be set for a predetermined location.

18. A non-transitory computer readable medium including executable instructions, that when executed by a processor cause the processor to perform an information providing method performed with a robot apparatus, the method comprising:
storing and subsequently retrieving from a computer program storage device cueing point information and user information,
said cueing point information including position information and level of care information associated with said position information,
said user information including identification information of a user and user-specific level of care information associated with the identification information of the user;
determining with the processor to issue a cue based on at least said cueing point information and said user information;
recognizing said user and a position of the user; and
issuing at least one of an audio cue and a visual cue when the processor decides to issue the cue, wherein
the determining is conducted by (a) identifying whether the position of the user identified by the recognizing is in a predetermined range of a corresponding cueing point based on the position information, (b) identifying the user-specific level of care information based on the identification information of the user identified by the recognizing, and (c) comparing the level of care information associated with the position information of the corresponding cueing point with the identified user-specific level of care information.

19. The non-transitory computer readable medium of claim 18, wherein
said determining step determines said user-specific level of care information based on a recognition made by the processor in said recognizing step.

20. The non-transitory computer readable medium of claim 18, wherein said method further comprising:
recording an environmental map in said computer program storage device, wherein cueing point information for corresponding cueing points are stored in association with predetermined regions within said environmental map.

21. The non-transitory computer readable medium of claim 20, wherein:

said recording includes recording an update of the environmental map, said update being triggered by at least one of a predetermined time period and a change in content in said environmental map.

22. The non-transitory computer readable medium of claim 18, wherein said method further comprising:
recognizing with the processor a behavior of said user, and
predicting a future behavior of said user based on a present behavior of said user as recognized by said processor; wherein
said determining step determines the cue to be given based on the future behavior of said user as predicted in said predicting step and a corresponding cueing point.

23. The non-transitory computer readable medium of claim 18, wherein:
the cue issued in said issuing being classified into one of a plurality of patterns including behavior patterns and time patterns.

24. The non-transitory computer readable medium of claim 18, wherein said method further comprising:
receiving from a portable wireless communication device a signal requesting a cueing point be set for a predetermined location.

\* \* \* \* \*